(12) United States Patent
Liu

(10) Patent No.: US 10,736,364 B2
(45) Date of Patent: Aug. 11, 2020

(54) KINEMATIC BRA FOR POSTURE RECOVERY AND THORACIC MOBILITY

(71) Applicant: IFGCURE HOLDINGS, LLC, Los Angeles, CA (US)

(72) Inventor: Stephen H Liu, Los Angeles, CA (US)

(73) Assignee: IFGCURE HOLDINGS, LLC, Los Angeles, CA (US)

( * ) Notice: Subject to any disclaimer, the term of this patent is extended or adjusted under 35 U.S.C. 154(b) by 0 days.

(21) Appl. No.: 16/368,588

(22) Filed: Mar. 28, 2019

(65) Prior Publication Data

US 2020/0008496 A1 Jan. 9, 2020

Related U.S. Application Data

(63) Continuation-in-part of application No. 16/147,639, filed on Sep. 29, 2018, and a continuation of application No. 16/125,453, filed on Sep. 7, 2018, which is a continuation-in-part of application No. 16/057,558, filed on Aug. 7, 2018, now abandoned, which is a continuation-in-part of application No. 16/029,567, filed on Jul. 7, 2018.

(Continued)

(51) Int. Cl.
*A41C 3/00* (2006.01)
*A61F 5/02* (2006.01)
*A41C 3/08* (2006.01)

(52) U.S. Cl.
CPC .............. *A41C 3/0064* (2013.01); *A41C 3/08* (2013.01); *A61F 5/026* (2013.01); *A41B 2300/22* (2013.01); *A41B 2400/32* (2013.01); *A41C 3/0028* (2013.01)

(58) Field of Classification Search
CPC ....... A41C 3/0064; A41C 3/08; A41C 3/0028; A41B 2300/22; A41B 2400/32; A61F 5/024; A61F 5/026; A61F 5/028
USPC ............ 450/2, 74, 75, 76, 93, 30, 7, 19, 83; 128/873, 874, 875
See application file for complete search history.

(56) References Cited

U.S. PATENT DOCUMENTS 162,580 A * 4/1875 Schandevyl ............. A41C 1/06
 450/27
1,075,348 A * 10/1913 Fritsch .................... A61F 5/028
 128/DIG. 19

(Continued)

*Primary Examiner* — Jameson D Collier
*Assistant Examiner* — Jocelyn Bravo
(74) *Attorney, Agent, or Firm* — Ferguson Case Orr Paterson

(57) ABSTRACT

A therapeutic posture correcting and chest expanding bra invention for improving posture and thoracic mobility, including a method of manufacture thereof in the posture recovery, chest expansion, shoulder and spine muscle rehabilitation, occupation risk prevention, anti-aging posture training and athletic enhancement space. A bra that is uniquely designed, manufactured and fabric woven to improve scapular kinematics and spinal biomechanics, and overall proprioceptive posture rebalance, correction and comfort that allows for breathability, functionality, range of motion, and a fashionable nature. The kinematic bra is uniquely designed and narrows the distance between the scapulae with proprioceptive shoulder muscle relaxation and spinal muscle activation, and, secondarily, allows for chest expansion to provide better breathing and overall improvement of women's health and wellness.

20 Claims, 7 Drawing Sheets

Related U.S. Application Data

(60) Provisional application No. 62/649,542, filed on Mar. 28, 2018.

(56) References Cited

U.S. PATENT DOCUMENTS

| | | | | |
|---|---|---|---|---|
| 1,129,515 | A * | 2/1915 | Perry | A41B 9/06 2/112 |
| 1,804,855 | A * | 5/1931 | Bollwine | A41C 3/0021 450/83 |
| 2,009,620 | A * | 7/1935 | Jackson | A41F 15/00 2/73 |
| 2,211,549 | A * | 8/1940 | Semons | A41C 3/08 2/114 |
| 2,310,855 | A * | 2/1943 | Manson | A41C 3/08 450/34 |
| 2,327,488 | A * | 8/1943 | Becker | A41C 3/0028 450/5 |
| 2,585,567 | A * | 2/1952 | Marin | A41C 3/08 2/73 |
| 2,591,462 | A * | 4/1952 | Mungo | A41C 3/00 450/2 |
| 2,800,659 | A * | 7/1957 | Hazard | A41C 1/06 450/27 |
| 2,881,764 | A * | 4/1959 | Verreault | A41C 3/00 450/59 |
| 3,066,676 | A * | 12/1962 | Kaupp | A41C 3/02 450/58 |
| 3,144,869 | A * | 8/1964 | Blair | A41C 3/00 450/74 |
| 3,430,632 | A * | 3/1969 | Emily | A41C 3/00 450/1 |
| 4,289,137 | A * | 9/1981 | Dell | A41C 3/02 2/67 |
| 4,341,219 | A * | 7/1982 | Kuznetz | A41C 3/0057 450/74 |
| 4,398,538 | A * | 8/1983 | Johnson | A41C 3/08 2/67 |
| 4,538,614 | A * | 9/1985 | Henderson | A41D 13/0017 2/1 |
| 4,741,719 | A * | 5/1988 | Wirth | A41D 13/0017 450/30 |
| 4,781,651 | A * | 11/1988 | Ekins | A41C 3/0057 450/25 |
| 4,816,005 | A * | 3/1989 | Braaten | A41C 3/0057 450/58 |
| 5,259,833 | A * | 11/1993 | Barnett | A61F 5/026 2/44 |
| 5,823,851 | A * | 10/1998 | Dicker | A41C 3/0057 450/2 |
| 5,839,942 | A * | 11/1998 | Miller | A41C 3/04 450/58 |
| 5,897,422 | A * | 4/1999 | McGee | A41C 3/00 2/73 |
| 5,968,003 | A * | 10/1999 | Sisson | A41C 3/0064 602/19 |
| 6,168,498 | B1 * | 1/2001 | Wagner | A41C 3/0057 450/1 |
| 6,280,287 | B1 * | 8/2001 | Keith | A41C 3/0028 450/1 |
| 6,530,820 | B1 * | 3/2003 | Katze | A41C 3/08 450/30 |
| 7,731,564 | B2 * | 6/2010 | Sanders | A41C 3/0057 450/39 |
| 7,914,473 | B2 * | 3/2011 | Josey | A63B 23/0244 600/594 |
| 7,922,682 | B2 * | 4/2011 | Bell | A41C 3/0064 128/874 |
| 8,465,341 | B2 * | 6/2013 | Shashy | A41C 3/0057 450/39 |
| 8,523,629 | B2 * | 9/2013 | Pundyk | A41C 3/0021 450/30 |
| 8,574,027 | B2 * | 11/2013 | Kipnes | A41D 1/22 2/73 |
| 8,900,032 | B2 * | 12/2014 | Punsal | A41C 3/122 450/17 |
| 8,915,765 | B2 * | 12/2014 | Chayet | A41C 3/06 450/66 |
| 9,326,553 | B1 * | 5/2016 | Ross | A41C 3/0064 |
| 9,370,206 | B1 * | 6/2016 | Ellington | A41C 3/0064 |
| 9,730,475 | B1 * | 8/2017 | Tomkoria | A41C 3/005 |
| 9,743,693 | B2 * | 8/2017 | Zambelli | A41F 15/00 |
| 10,201,192 | B1 * | 2/2019 | Lott | A41C 3/0057 |
| 10,206,436 | B1 * | 2/2019 | Wooley-Scheiman | A41C 3/0057 |
| 10,213,331 | B1 * | 2/2019 | Weiler | A61F 5/02 |
| 2002/0031978 | A1 * | 3/2002 | Heroff | A41C 3/08 450/30 |
| 2004/0137821 | A1 * | 7/2004 | Sandroussi | A41C 3/0014 450/34 |
| 2006/0194509 | A1 * | 8/2006 | Patterson | A41C 3/0064 450/54 |
| 2007/0281586 | A1 * | 12/2007 | Pritchard | A41C 3/08 450/37 |
| 2008/0194179 | A1 * | 8/2008 | Leung | A41C 3/08 450/31 |
| 2009/0081924 | A1 * | 3/2009 | Puyaubreau | A41C 3/0057 450/39 |
| 2009/0209172 | A1 * | 8/2009 | Getz | A41C 1/06 450/7 |
| 2009/0258572 | A1 * | 10/2009 | Chayo | A41C 3/0028 450/39 |
| 2009/0259159 | A1 * | 10/2009 | Bell | A41C 3/0064 602/75 |
| 2009/0265830 | A1 * | 10/2009 | Hendrickson | A41D 1/215 2/104 |
| 2009/0265831 | A1 * | 10/2009 | Hendrickson | A41C 3/04 2/104 |
| 2009/0270013 | A1 * | 10/2009 | Clair | A41C 3/08 450/30 |
| 2010/0298914 | A1 * | 11/2010 | Rosenbaum | A61F 7/00 607/108 |
| 2011/0214216 | A1 * | 9/2011 | Zarabi | A41D 27/02 2/69 |
| 2011/0275276 | A1 * | 11/2011 | Shashy | A41C 3/0057 450/76 |
| 2012/0021669 | A1 * | 1/2012 | Johnstone | A41C 3/0028 450/58 |
| 2012/0040588 | A1 * | 2/2012 | Steele | A41C 3/0057 450/74 |
| 2012/0122370 | A1 * | 5/2012 | Heath | A41C 3/0057 450/80 |
| 2012/0142252 | A1 * | 6/2012 | Hopkins | A41C 3/08 450/31 |
| 2012/0149277 | A1 * | 6/2012 | Moses-Jones | A41C 3/0028 450/41 |
| 2012/0244782 | A1 * | 9/2012 | Pundyk | A41C 3/0021 450/70 |
| 2013/0303049 | A1 * | 11/2013 | Jackson | A41C 3/08 450/30 |
| 2014/0087625 | A1 * | 3/2014 | Ironi | A41C 3/04 450/36 |
| 2014/0141692 | A1 * | 5/2014 | Yuasa | A41C 3/08 450/30 |
| 2014/0235139 | A1 * | 8/2014 | Chayet | A41C 1/003 450/75 |
| 2015/0056890 | A1 * | 2/2015 | Black | A41C 3/0057 450/86 |
| 2015/0072591 | A1 * | 3/2015 | Almog | A41C 3/12 450/75 |
| 2016/0015090 | A1 * | 1/2016 | Mazourik | A41C 3/0028 450/39 |
| 2016/0037829 | A1 * | 2/2016 | Cronin | A41C 3/0021 450/59 |
| 2016/0044971 | A1 * | 2/2016 | Randall | A41C 3/142 450/39 |
| 2016/0058075 | A1 * | 3/2016 | Dandapure | A41C 3/00 450/39 |

(56) References Cited

U.S. PATENT DOCUMENTS

| | | | |
|---|---|---|---|
| 2016/0081398 A1* | 3/2016 | Tempesta | A41C 3/0057 |
| | | | 450/70 |
| 2016/0206015 A1* | 7/2016 | Zambelli | A41F 15/00 |
| 2016/0374405 A1* | 12/2016 | Washington | A41C 1/02 |
| | | | 450/76 |
| 2017/0035130 A1* | 2/2017 | Hazzard | A41C 3/0028 |
| 2017/0202274 A1* | 7/2017 | Blackwell | A41C 3/0064 |
| 2017/0208873 A1* | 7/2017 | Farneti | A41D 13/0017 |
| 2017/0273365 A1* | 9/2017 | Muhlenfeld | A41B 1/08 |
| 2018/0014579 A1* | 1/2018 | Gumlaw | A41C 3/0064 |

\* cited by examiner

KINEMATIC BRA FOR POSTURE RECOVERY AND THORACIC MOBILITY

CROSS REFERENCE TO RELATED APPLICATIONS

This PCT international application claims priority to the following applications: U.S. patent application Ser. No. 16/147,639 entitled POSTURE RECOVERY THERAPEUTIC BRA filed Sep. 7, 2018, which is a continuation of U.S. patent application Ser. No. 16/125,453 entitled POSTURE, PERFORMANCE, RECOVERY (PPR) BRA filed Sep. 4, 2018, which is a continuation-in-part application of U.S. patent application Ser. No. 16/057,558 entitled POSTURE, PERFORMANCE, RECOVERY (PPR) BRA filed on Aug. 7, 2018, which is a continuation-in-part application of U.S. patent application Ser. No. 16/029,567 entitled POSTURE, PERFORMANCE, RECOVERY (PPR) BRA filed on Jul. 7, 2018, which claims priority to U.S. Provisional Patent Application No. 62/649,542, entitled POSTURAL RECOVERY BRA, filed Mar. 28, 2018. The contents of all applications are hereby incorporated by reference in their entirety.

FIELD OF THE INVENTION

It is an object of the present invention to provide a comfortable and proprioceptive woven, multi-layer blended fabric, therapeutic posture correcting and chest expanding kinematic bra that corrects a wearer's posture using anatomically correct movement that allows for spinal, shoulder, and chest mobility, improves chest expansion, is breathable and aesthetically pleasing to promote patient compliance, and is not so tight as to be hot and uncomfortable to wear.

The present invention is directed to a bra using spinal muscle, scapular kinematics, and proprioception for posture recovery, chest expansion, and thoracic mobility. The bra is used for daily wear to improve and prevent progressive slouching, improve thoracic mobility post breast surgery, provide for support of large and dense breasts, and help with: activities of daily living (ADL); post-surgery shoulder recovery; occupation risk prevention; and athletic recovery, among many other industry and healthcare applications. The multi-panel, multi-layered proprioceptive bra is uniquely designed to better women's health through the above described functionalities.

BACKGROUND OF THE INVENTION

Posture correcting garments and bras are known and have been used for several years; primarily with a goal of stimulating body muscles into better alignment and posture resulting in a slight S-shape of the spine—the orthopedic gold standard for perfect spinal alignment. The importance of having good posture is a well-known and a long-accepted priority among healthcare professionals and even non-experts in the field. Good posture is vital for overall health (prevention of back, shoulder, neck pain, etc.) and vital for athletic performance; as poor posture or form during dynamic athletic activities results in inefficient biomechanics and body movement. Poor posture is typically observationally categorized by 'shoulders rolled forward', 'a forward curvature in the thoracic spine', and/or a 'left or right lean of the thoracic spine. In addition, inefficient body movement caused by poor posture prevents full utilization of skeleto-muscular range of motion and strength which commonly causes repetitive injury. Typical treatment methods for those suffering from back, neck, and other pain include chiropractors, physical therapy, or orthopedic surgeon evaluation and possible treatment. Such medical procedures to correct poor posture involve injections, medications, rehabilitation, and typically as a last resort—surgical correction. As many cannot afford the cost or time of extensive and costly chiropractor or physical therapy treatment, there exists a need for alternative and affordable apparel therapy methods and systems, with the therapeutic posture correcting and chest expanding bra being a first and appropriate choice, to:

a) Improve spinal and shoulder proprioception,
b) Improve spinal and shoulder kinematics,
c) Provide comfort, function, and pain relief,
d) Increase compliance for daily wear,
e) Improve thoracic mobility, and
f) Improve chest expansion to allow for better breathing.

The first attempts at using a wearable garment to refine biomechanical factors that influence posture and kinesthetic states was originated in the 1970's within the Soviet space program, in order to counteract the effects of long-term weightlessness. This device, known as the Adeli suit, is used to treat pediatric patients with postural disabilities due to neurological conditions that lead to brain damage or spinal cord injury. Its design is relatively simple, involving elastic connections between the primary joints, specifically to target positions of antagonistic muscle pairs. However, there are still many other of ways and degrees to which the body can become imbalanced due to disruptions in the kinetic chain of muscle activation.

Muscles devoted substantially to the concepts of balance and posture are sometimes referred to as gravity and anti-gravity muscles; they are the tools that provide upright organisms with the ability to maintain the center-of-gravity (COG) within a stable base of support. Upright balance is attained when a vertical line follows from the center-of-gravity, directly down through this base of support. Any imbalance will cause compensatory abnormalities which will affect alignment within the body's whole musculoskeletal system. Optimized postural alignment is crucial in counteracting the constant downward gravitational forces opposing the body. When the upright force of musculoskeletal architecture and the downward force of gravity are balanced, muscles are able to function with the least amount of work, i.e. peak efficiency.

When the upright body holds better posture, smaller amounts of stress and strain are placed on the muscles, ligaments and bones thereby enhancing their efficiency and increasing bone density and muscle mass in the long term. Opposing the force of gravity, the so-called anti-gravity muscles assist to maintain an upright, balanced posture. For the upper body and the muscles of the back, these muscles include the trapezius, the rhomboids, and several smaller groups around the shoulder such as the teres minor and subscapularis. Additionally, the cervical-occipital muscle groups maintain the head in an erect position, thereby preventing it from rolling forward. These muscle groups simultaneously play an important role in the proprioception process, with proprioceptors in the dermal surface sending key information about pressure in the feet to the antigravity muscles through the nervous system. Any weakening of these muscles combined with the continuously working gravitational forces leads to poor postural stability, which affects muscle function. Postural alignment is essential to maintain normal length-tension relationships of the muscles especially during dynamic posture, determining the ease with which the body segments align themselves throughout movement. Any disruptions to this alignment throw the kinetic chain of the body off balance, making the person susceptible to a host of injuries. Understanding our limitations in controlling the effect gravitational forces have on the muscles and structure should form the basis of treatment programs.

As one treatment option, compression-based shirts and tight-fitting girdles were created to fill the burgeoning need of postural correction. In addition, several posture and sports bras were also created to assist the breasts and provide wearers with a comfortable way to support and enhance posture. These bras take a variety of approaches to posture correction, as some focused on simultaneously supporting and visually enhancing the breasts using breast cups and elastomeric material and straps. The specific bra in discussion, (Mazourik) US20160015090A1, claims functional support but, in reality, is just a "push-up" bra with thinly valid orthopedic functionality. Other bras currently on the market are very much like posture shirts and girdles, and they typically contain vertical straps that do not mimic natural anatomical movement. One bra in particular, (Fenske) US20090126084, uses shoulder cap straps to grab the skin at the area of the pectoral muscles. While this may provide some form of posture correction, it does not do so in an anatomically correct method, and despite claims of comfort, cannot be that comfortable, as multiple straps unnaturally pulling on your shoulders does not make for easy and daily wear. More specifically, vertical straps take the wrong approach to correcting a wearer's posture—namely, the straps do not focus on proprioceptive correction to achieve biomechanically correct postural alignment but instead focus on force. This force creates an unnatural alignment that may push a wearer's shoulders backwards in an outward appearance of better posture but in reality, doesn't achieve much short term or long-term success. Natural posture alignment in the thoracic and lumbar spine is achieved when posterior muscle groups (i.e. trapezius, rhomboids, latissimus dorsi, and erector spinae) and anterior muscle groups (serratus anterior, etc.) are both exerting the same amount of force, thus allowing the body to be balanced. Therefore, garments created in this space should target natural (proprioceptive) muscle re-balancing; however, current and previous garments or devices were not able to fully achieve this goal due to several limitations, including the one listed above.

Further to this idea, the vertical straps that most posture garments utilize end at the bottom of the buttocks, contributing to the unnatural pull that forces the shoulders back into an improper and unnatural position that does not mimic natural anatomical movement. The corresponding picture would be someone grabbing the bottom of one's shirt from the back and pulling it downwards and tucking it underneath one's glutes; this would certainly force one's shoulders back and straighten one's posture, but it would also align the posture in a constrained or compressive formation and prove to be uncomfortable, with poor compliance, and a challenge to wear at work or in occupation. For instance, one shirt of this kind was made from a cotton body with elastic straps that were attached at the front of each shoulder, ran over the back parallel to the spine, and connected at the bottom seam. That same shirt was not only anatomically incorrect, it was also extremely tight (made from a Lycra Spandex material), thus not breathable and uncomfortable.

Other bras, such as Dicker (U.S. Pat. No. 5,823,851), use both an over-shoulder harness that is interconnected by a cross brace and contains a support belt that encircles the wearer's torso. One can imagine how complex this would be just to put on, not to mention how burdensome it would be to carry around on your body all day. Compliance is already out the window. Back and breast support posture bras cannot be achieved through compromising form, ease of wear, proper anatomical methods, and fashion, among other things, otherwise—people just won't wear them.

Known methods and systems include US20090062704 and US20110213283 directed to a shirt type garment made from a cotton body with elastic straps attached at the front of each shoulder and running over the back parallel to the spine and connected at a seam toward the bottom of the shirt. These shirts are made from a Lycra® Spandex® material with mesh and a woven stretch fabric. Similar systems utilize a Lycra® Spandex® combination material to provide structural stability, compression, and an athletic garment look. However, such material is not breathable. In order to effectively gain stability from and in the body for proprioception, and to correct posture imbalance; Lycra® Spandex® garments must be worn extremely tight to the body leading to discomfort.

Other known methods and systems include US20160015090 (Mazourik mentioned above), US20090126084 (Fenske), and U.S. Pat. No. 5,823,851 (Dicker). The description and limitations of each has already been discussed at length above.

The present invention differs from previous and current posture garments or devices in that it utilizes natural dynamic (muscular) and static (scapular kinetics) combined proprioception to alter spinal biomechanics and scapular kinematics for posture restoration, upright stance restoration, and improved thoracic mobility. An organism naturally uses proprioception to maintain an internal model of its body's orientation in space, a sort of mental avatar representing the mind's best guess as to how its physical limbs are moving. When the primary motor cortex signals the muscles to fire, it also emits an efference signal, also known as a corollary discharge. This second signal has been hypothesized to suppress the subsequent firing of sensory cortex networks when they are inevitably stimulated by the aforementioned motor movement. Therapeutically applied proprioception can be explained by intensifying and subsequently normalizing the afferent proprioceptive mobility-controlling input.

Rather than utilizing vertical straps, one form of the proprioceptive induction technique is the utilization of the posterior scapular straps/elastic tension band construct that re-aligns the scapulae from a protracted (forward) position to a retracted (horizontal) position. A horizontal motion that moves the scapula towards the spine induces spinal extension and re-aligns the head on top of the spine. This natural movement induces erector spinal muscle activation (arching the spine), relaxation of the trapezius muscle, and posterior moving of the head to better align with the spine. This method of postural correction is natural and sustainable because it alters both spinal and scapular biomechanics to recover a wearer's posture and then passively influences the posture after it is corrected. This is achieved due to the natural tension that the scapular straps exert on the wearer's scapulae, which retrains spinal and scapular muscles to ensure the wearer is in an upright posture and correct postural form without the force of a vertical strap constantly pulling over the shoulder and down to the buttock's region.

Additional systems include U.S. Pat. Nos. 4,202,327, 4,957,103, 5,158,531, 5,451,200, 5,599,286, 5,718,670, 6,102,879, 6,213,922, 6,440,094, 6,676,617, 6,936,021, 7,134,969, 7,153,246, 7,395,557, 7,662,121, 7,871,388, 8,047,893, 8,083,693, 8,308,670, 8,516,614, 8,556,840, 8,795,213, 8,795,215, 8,887,315, 8,905,956, 8,910,317, 8,932,236, 9,009,863, 9,167,854, 9,168,167, 9,226,534, 9,439,459, 9,445,932, 9,456,919, 9,504,280, 9,883,703, 9,931,236, US20040107479, US20050197607, US20060000478A1, US20080134409A1, US20090062704, US20100192274A1, US20120078149, US20120174282, US20130047313, US20130053744, US20130090521, US20130103079, US20140058307, US20140100501, US20140221893 and US20150040286A1.

However, none of the prior art references provide a proprioceptive bra that efficiently and effectively corrects a wearer's posture. None of the prior art references provide data for a narrowing of the distance between the shoulder blades in a resting position or a narrowing of the distance between the scapula to the spinous process while using a bra. There exists a need for a proprioceptive woven fabric posture bra that corrects a wearer's posture and improves chest expansion and thoracic mobility, by narrowing the distance between right and left scapula using proprioceptive muscle retraction, using anatomically correct movement that allows for shoulder mobility, is breathable and aesthetically pleasing to promote patient compliance, and is not so tight as to be hot and uncomfortable to wear.

Accordingly, the present invention is directed to solving all of these problems.

SUMMARY OF THE INVENTION

It is an object of the present invention to provide a therapeutic bra that efficiently corrects and improves a wearer's posture, spinal alignment, chest expansion, and head position. It is an object of the present invention to provide an improved spinal biomechanics bra that brings both shoulder blades (scapula) closer to the spine, or closer together, and that corrects a wearer's posture while improving chest expansion for better breathing.

It is an object of the present invention to provide a comfortable and proprioceptive woven fabric posture re-balance bra that corrects a wearer's posture using anatomically correct movement that allows for spinal, shoulder, and chest mobility, is breathable and aesthetically pleasing to promote patient compliance, and is not so tight as to be hot and uncomfortable to wear.

It is an object of the present invention to achieve mainstream consumer adoption in order to promote compliance and thus be commercially successful, and to be both functional and fashionable (or at least, not unsightly); and to successfully reach a wide swath of users who may need such therapy to prevent or assist in correcting present and/or future back and shoulder symptoms. The spectrum of users ranges from those who suffer from occupational risk prevention seen in many industries to professionals, teenage girls, the aging population, as well as women with large or dense breasts complaining of neck and back discomfort.

Objects of the invention are achieved by providing a stylish, comfortable therapeutic posture correcting bra, comprising a front panel and a rear panel connected along a left and right seam; a chest band connected circumferentially to the front and rear panel; a left and right shoulder strap connecting the front panel to the rear panel, with the left and right shoulder strap both comprised of an anterior portion and a posterior, scapular, portion; and an elastic strap connecting the left posterior scapular portion to the right posterior scapular portion.

In certain embodiments, the front and rear panel comprise two or more polyester fabric layers.

In certain embodiments, the elastic band comprises three fabric layers, with a combination of polyester fabric, tensioning fabric (e.g., elastic), and polyester fabric, whereby the tensioning fabric is the key component for posture correction and the polyester fabric is just a self to provide greater comfort and aesthetics. The mesh component highlights the unique horizontal 'see-saw' tension that the therapeutic bra provides, which is a vertically, relatively, inelastic bra that is pre-tensioned and stretches horizontally for comfort and function to correct posture.

In certain embodiments, the chest band and left and right straps are both single, double, or triple-layered with any combination of mesh/fabric or mesh/mesh.

In certain embodiments, left and right posterior shoulder straps can be full-length and connect directly to the chest band with no rear panel in-between, while still configured to achieve the same purposes of posture recovery, spinal extension, and thoracic mobility such as chest expansion and chest extension.

In certain embodiments, the left and right anterior shoulder straps can be full-length and connect directly to the chest band, forming an upside-down-triangle-shaped double-mesh covering panel that also connects to the chest band, while still configured to achieve the same purposes of posture recovery, spinal extension, and thoracic mobility such as chest expansion and chest extension.

In certain embodiments, the front panel can be low cut for aesthetic purposes.

In certain embodiments, the elastic strap comes pretensioned, which can be accomplished by tensioning the elastic strap prior to attaching it to the rest of the bra, and with a various width pending on the size of the wearer (usually one to four inches).

In certain embodiments, at least one horizontally spaced pretensioned elastic strap is provided. The strap is either sewn into the exterior or interior of the bra.

In certain embodiments, the posterior shoulder mesh strap and elastic strap integration can be sewn into any existing suitable front panel bra.

In certain embodiments, the posterior shoulder straps are configured to primarily bring the shoulder blades closer to the spine and secondarily expand the rib cage for ease of breathing and comfort fit of the user. These straps lie along the borders of the scapula and embody the entire scapula fossa for better proprioception and movements of the scapula.

In certain embodiments, the elastic strap is configured to pull a wearer's thoracic towards the anterior of the wearer, thus opening up the ribcage of the wearer for ease of breathing and comfort of fit.

In certain embodiments, the elastic strap is configured to provide a see-saw motion resulting firstly in improved scapular proprioceptive retraction and secondarily in rib cage expansion for better breathing.

In certain embodiments, the expansive chest band located in the lateral portions of the chest combine with the elastic strap to simultaneously allow for expansion of the rib cage during inhalation as well as the pulling of the scapula back into proper alignment, which allows for an easier fit while still maintaining proper postural correction.

In certain embodiments, the elastic strap can be positioned to range from a superior angle of the scapular to the inferior angle of the scapula.

In certain embodiments, in use, the elastic strap extends between about or below the nuchal and the center of the back of a wearer. In certain embodiments, in use, the elastic strap lies along, and/or aside the scapula of a wearer, from top to bottom.

In certain embodiments, the elastic strap is provided when maximally stretched, i.e., in a pre-tensioned state.

In certain embodiments, the elastic strap provides posterior pull to the bra wearer and places the bra wearer's ribcage into proper alignment by providing horizontal stretch and pulling towards the center of the wearer's spine.

In certain embodiments, the elastic strap (ES) is configured to provide a see-saw motion due to the vertical inelasticity and horizontal elasticity, which leads to behavior such as expanding and contracting in a horizontal fashion, which results in improved proprioceptive scapular retraction for better posture and in rib cage expansion for better breathing.

In certain embodiments, the front panel of the bra may include two cup portions, the two cup portions able to provide support for the wearer's breasts.

In certain embodiments, the anterior shoulder straps have a width within the range of about 1-4 inches, while the posterior shoulder straps have varying widths between 1-10 inches. In certain embodiments, all straps can be of various widths depending upon the size of the wearer.

In certain embodiments, the bra contains an elastic strap that acts as a proprioceptive mechanism to correct a wearer's posture. In certain embodiments, recovery of a wearer's posture is corrected biomechanically. In certain embodiments, the bra corrects a wearer's posture by extending the lumbar spine (spinal erector activation), narrowing the scapular distance by at least 5 mm (altering the kinematics), secondarily pulling the shoulders of the wearer to the posterior, and bringing the head on top of the spine, thereby reducing the tension on the shoulder muscles.

In certain embodiments, the back portion of the bra or combination of front and back portions can be standalone, sewn or attached into any existing shirt or top garment as a shelf bra, or be sewn into a garment during the garment production process and come as an inner layer of a finished outer garment.

In certain embodiments, the bra is used for medical and non-medical purposes to improve the wearer's posture, provide spinal support, and help prevent posture deterioration through aging.

In certain embodiments, the bra improves recovery from shoulder surgery or injury, physical therapy, athletic training, athletic recovery, athletic performance, and breathing.

In certain embodiments, the bra improves women's health issues, namely chronic round shoulders due to large or dense breasts and back pain during pregnancy.

In certain embodiments, the bra corrects the wearer's posture by 1) narrowing the distance between the left and right scapula, 2) pushing the clavicle back due to the design of the anterior shoulder straps' shape and 3) inducing spinal extension with spinal muscle activation.

In certain embodiments, the bra contains anti-microbial moisture wicking and protects against ultra-violet (UV) rays, In certain embodiments, the bra further includes a single or double mesh layer provided underneath the poly elastic strap portion and configured to provide improved shoulder kinematics and comfort to the wearer.

In certain embodiments, the bra improves the wearer's posture by narrowing the distance at least 5 mm between the left and right scapula.

In certain embodiments, the front portion of the bra is detachable and interchangeable from the posterior left and right shoulder straps. In certain embodiments, the front portion of the bra includes multiple styles, mesh layering, and includes customizable options.

In certain embodiments, the chest band allows for ease of breathing and a more comfortable fit, and it may have one to three layers of fabric, with or without power mesh.

In certain embodiments, the chest band is of various widths and lengths pending on the wearer's size and allows for improved expansive movement of the rib cage.

In certain embodiments, the bra provides postural support to a wearer suffering from the following: rounded shoulders, scapular dyskinesis, kyphosis, forward head, lordosis, scoliosis, cervical spine injury, shoulder pathologies, pregnancy, large dense breast women with chronic round shoulders, aging posture, neck pathologies, chronic headaches, acromioclavicular (AC) joint separation, spinal and shoulder muscle weakness, shoulder rehabilitation, shoulder recovery, shoulder training, cervical/occipital neuralgia, frozen shoulder, and scapular winging.

In certain embodiments, the bra corrects the wearer's posture through a form of direct physical therapy and indirectly through proprioceptive feedback.

In certain embodiments, the bra provides comfort and allows for a full range of motion for the wearer, with a minimized restriction of movement.

In certain embodiments, the garment corrects the wearer's posture by narrowing the shoulder blades, essentially moving the head to a posterior position, with less tension on the neck muscles, and placing the scapula in the more retracted position.

In certain embodiments, the bra is used for medical and non-medical uses.

In certain embodiments, the bra is used for sports training and recovery, posture correction and training, spinal therapy, breast surgery therapy, pregnancy wear, large-dense breasts, industry and healthcare workforce wear, activewear, and combinations thereof.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

DETAILED DESCRIPTION OF THE INVENTION

Figure 1:
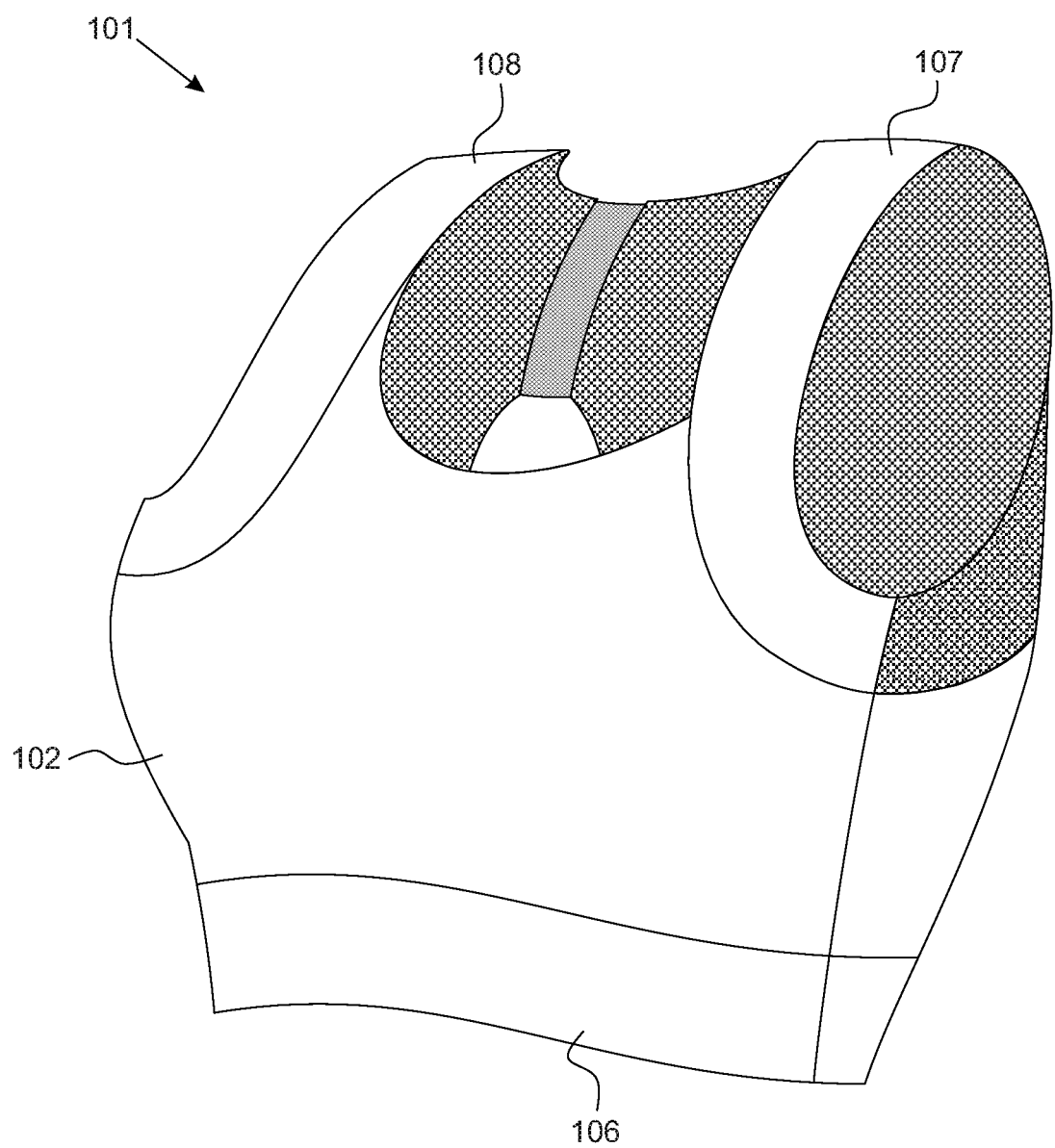
FIG. 1 is a front perspective view of the therapeutic bra.

This application incorporates by reference U.S. patent application Ser. No. 16/024,881 entitled POSTURE, PERFORMANCE, RECOVERY GARMENT DEVICE SYSTEM. The contents of this application are incorporated by reference herein in its entirety.

The present invention is a wearable device manufactured garment that accounts for the limitations of the currently made bra garments and utilizes a unique fabric design and construction method that involves multiple-layer blend fabric and multiple panels, pre-tensioned straps, and a chest band to improve spinal biomechanics and scapular kinematics for better back support, better posture, increased chest expansion, and improved thoracic mobility. The unique invention design includes an elastic pre-tensioned strap that contributes horizontal stretch to achieve proprioceptive postural correction and spinal and shoulder muscle rebalance. The other components include one or more shoulder straps, a chest band, and front and rear panels. The garment is designed to be worn by a user in the form of a bra, thus mitigating the issue of an unsightly garment that users wouldn't want to wear as their only layer. The bra is also customizable, fashionable, and breathable.

The garment also improves upon previous posture garments through its flexible nature, namely the ability to act as a garment addendum device, i.e. the posterior part of the bra can be sewn into any existing suitable bra. It achieves this flexibility while also solving the issues of shoulder restriction and non-breathability by allowing a full range of motion. The construction of prior garments did not allow for full forward range of motion due to the 'FIG. 8' or 'horse collar' nature of the loop, which was closed and had an inelastic seam, or the anatomically incorrect methods of construction that use compression or straps. The inventive garment also narrows the distance between the shoulder blades for the purposes of posture correction. The inventive garment also doesn't utilize harnesses, braces, cap straps, or any other previously incorrectly used method of posture correcting bra that pulled a wearer's shoulders back in the wrong anatomical fashion.

One posture correcting feature of the garment is the utilization of blending fabrics to achieve pre-tensioning effects, and to induce tension to due various levels of elasticity, of improved scapular kinematics by moving the shoulder blades closer to the spine. Accordingly, the nature of the fabric and design must change from previously invented bras to achieve proper postural tension, the details of which are highlighted below.

The woven nature of the shoulder strap fabric provides a style benefit, which is the elimination of the typical, unsightly seam construction of previous flat-lock construction posture correction garments. As mentioned above, the shoulder strap shape is limited in length due to the smaller nature of the bra versus a shirt. The garment also allows for customizability, as, in some embodiments, the front part of the bra can be fully detachable from the back, which provides additional optionality in the form of variable support for both front and back. The front panel of the bra comes in full coverage, flat front, or triangle cut, accounting for both style purposes and variation in needed support (larger vs. smaller breasts). The interchangeable nature of the bra does not change the amount of pressure that the bra back provides to the shoulders and thoracic for proprioceptive correction, thus adding a unique benefit without the drawbacks of a lesser product. The attachment points are on the upper straps and the side seams.

There are no lower straps, but rather seams included on both the front and back of the bra to provide support to the curve of the back (i.e. allowing forward and backward movement such as bending). The side seams are connected to a lower chest band that all combines to further contribute to proprioceptive posture correction by pulling the bra towards the anterior of the wearer's body. Furthermore, the bra of the present invention is easier to keep on than traditional bras, since the chest band opens up the rib cage, thus allowing the wearer to breathe more easily. By contrast, traditional bras are one piece, providing uncomfortable 360-degree compression.

The main posture correcting feature of the bra are the posterior scapular straps that pull the scapula of the wearer closer to the spine combined with the elastic strap that sits between both scapular straps and provides horizontal stretch, with the tailored elastic pulling all the tension towards the center of the spine and helping pull the shoulder blades into proper alignment. Specifically, the posterior strap/elastic strap combination achieves posture correction through a proprioceptive manner that involves creating a parallel amount of tension in the body's anatomical musculature, helping active and passive scapular motion of retraction and protraction into better anatomical alignment as well as improved rib cage flexibility and ease of expansion. Once the patient is in correct postural alignment, the bra automatically relieves all tension in the garment. Thus, the wearer will barely notice the device once the wearer has achieved the muscle memory of correct posture. As measured empirically, utilizing the Scapula Lennie test, the bra presents, in average, about an 11 mm (range of between about 5 mm and about 25 mm) narrowing of the distance between the left and right scapula. Thus, in certain embodiments, the herein disclosed bra affects at least about a 5 mm narrowing of the distance between the left and right scapula.

Figure 5A:
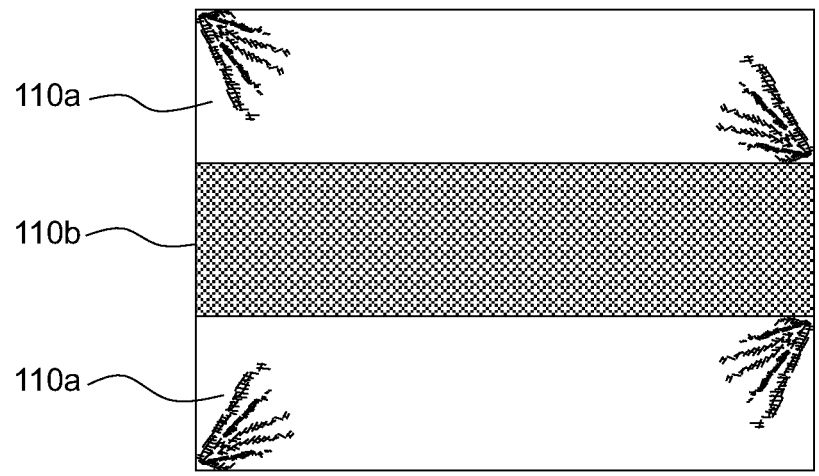
FIG. 5a is a view of the triple layered fabric comprising the elastic strap of FIGS. 2 and 4
Figure 5B:
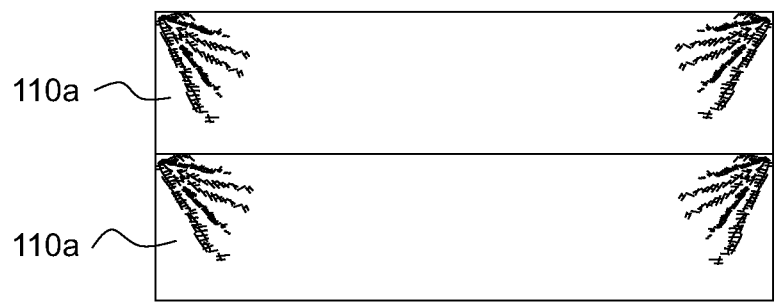
FIG. 5b is a view of the double layered fabric of FIGS. 1-4
FIGS. 6a and 6b are side views showing the posture correcting and chest expanding properties of the therapeutic bra versus a normal bra.

FIG. 1 depicts the therapeutic and chest expanding bra (101) front portion, with a front panel (115) connecting to a chest band (106) and a left shoulder strap (107) and a right shoulder strap (108). The front panel depicted here is a double-layered fabric (110a), as shown in FIG. 5B, while the chest band is a triple-layered fabric, as shown in FIG. 5A, with mesh sandwiched in-between poly fabric. The chest band can also be double-layered (110a), depending on the functional purposes.

Figure 2:
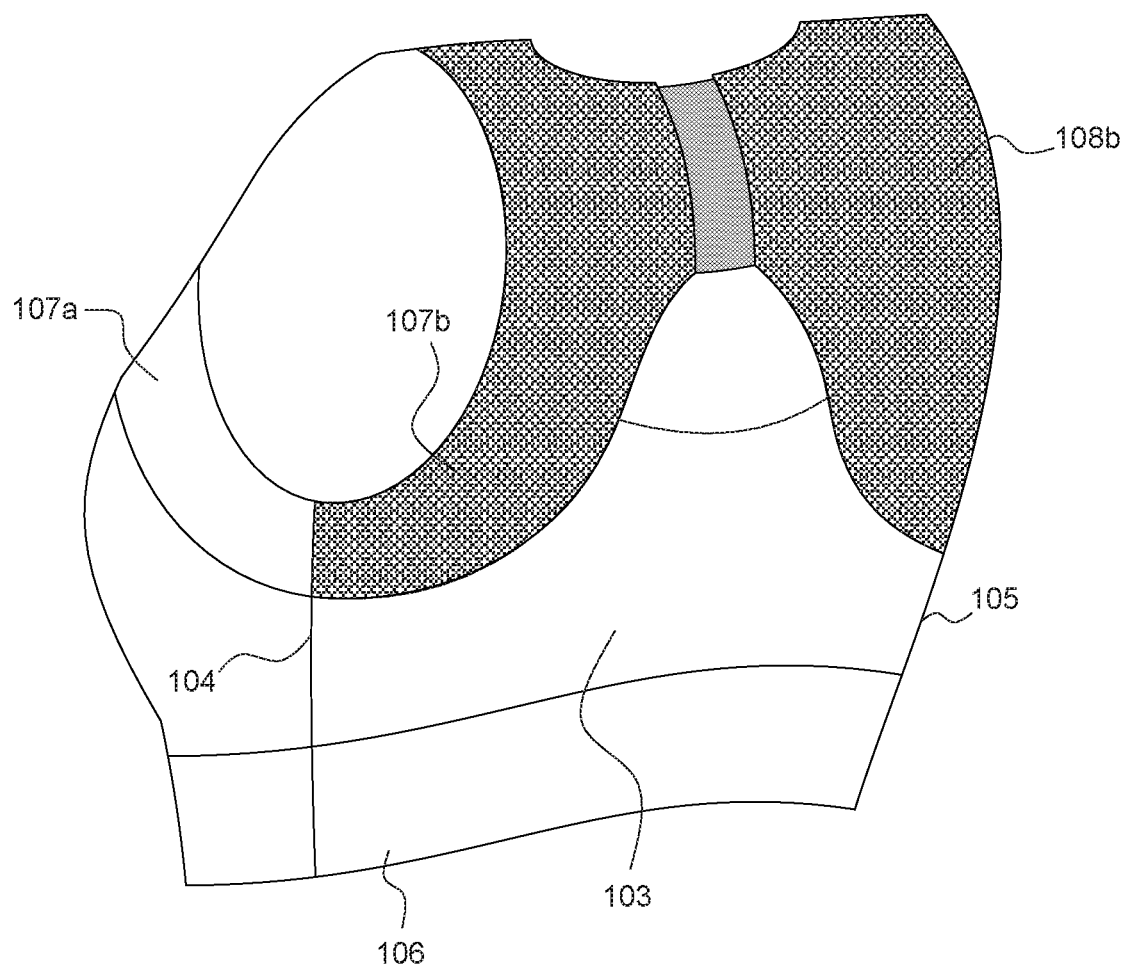
FIG. 2 is a rear perspective view of the therapeutic bra.
Figure 3:
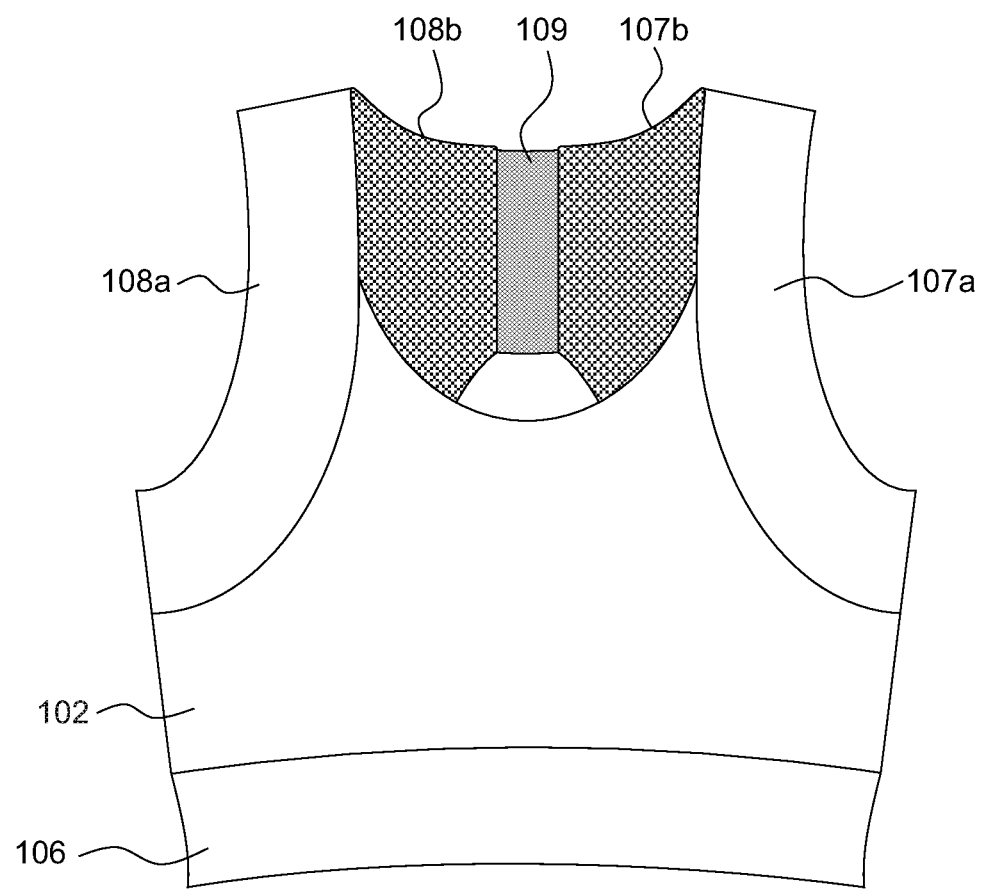
FIG. 3 is a front view of the therapeutic bra.
Figure 4:
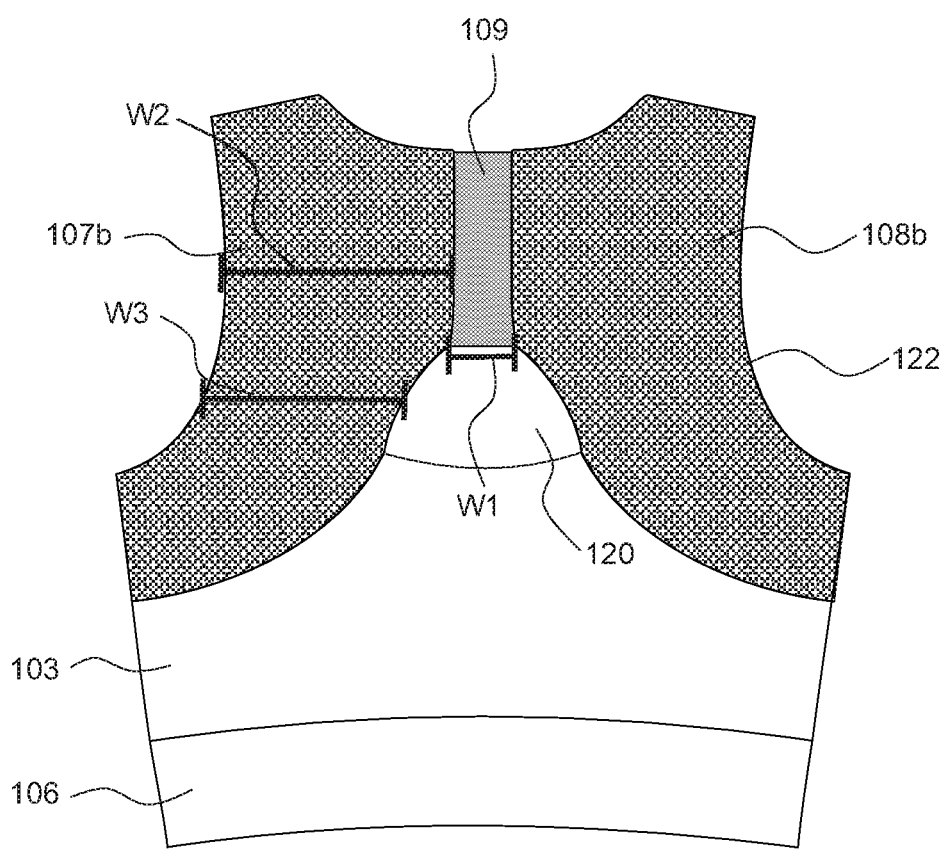
FIG. 4 is a rear view of the therapeutic bra.

In FIG. 3, the left (107) and right (108) shoulder straps are further shown to be split up into a left anterior portion (107a) and a right anterior portion (108a), with the left anterior portion connected via seam to a left posterior scapular portion (107b) depicted in FIGS. 2 and 4 and the right anterior portion connected via seam to a right posterior scapular portion (108b) depicted in FIGS. 2 and 4. The left (107a) and right (108a) anterior straps are a double-layered fabric, with the top layer being polyester and the bottom layer being a power mesh that provides additional support and tension for posture correction. The left (107b) and right (108b) posterior scapular straps, on the other hand, are a double-layered mesh, to provide additional tension and horizontal pull to bring the scapula closer to the spine of a wearer and thus put the wearer in proper postural alignment.

FIG. 2. depicts a rear perspective view of the therapeutic bra (101), which has the posterior straps (107b and 108b) connected to a rear panel (103), with the rear panel (103) connected to the same chest band (106) the front panel is connected to. FIG. 2 also shows the left seam (104) and right seam (105) that connects the front panel (102) to the rear panel (103). The rear panel (103) is also a double-layered fabric (110a) in this embodiment. As further shown in the embodiment of FIG. 2, posterior straps (107b and 108b) may connect to anterior straps (107a and 108a), respectively, in two locations at opposite ends of shoulder straps (107 and 108).

FIG. 4 further depicts the back of the therapeutic bra, also showing an elastic strap (109) that sits in-between the two posterior scapular straps (107b and 108b) and provides the strongest amount of tension and pull to correct posture. The elastic strap (109) has a triple-layered fabric construction of polyester (110a), elastic (110b), and polyester (110a), with the polyester portions acting as a self for comfort and aesthetic purposes. Elastic strap (109) comprises a top and a bottom surface that are substantially parallel and a left and a right surface that are substantially parallel, wherein the left surface is entirely connected to the left posterior portion (107b) and the right surface is entirely connected to the right posterior portion (108b). The right and left surfaces of elastic strap (109) each have an equal length and the top and bottom surfaces each have an equal width (W1) that is less than the length of the right and left surfaces. In the embodiment shown in FIG. 4, a gap (120) is formed between left posterior portion (107b), right posterior portion (108b), elastic strap (109), and rear panel (103). In one embodiment, left posterior portion (107b) is to the left of gap (120) and defines a left curved border of gap (120), right posterior portion (108b) is to the right of gap (120) and defines a right curved border of gap (120), elastic strap (109) is above gap (120) and defines a top border of gap (120), and rear panel (103) is below gap (120) and defines a curved bottom border of gap (120) such that the bottom surface of elastic strap (109) is directly above rear panel (103). As further shown in the embodiment of FIG. 4, right posterior portion (108b) of right shoulder strap (108) has different widths, including W2 and W3, wherein W2 extends perpendicularly to a midline of the bra from the right surface of elastic strap (109) to an armhole (122) in right shoulder strap (108), and W3 extends perpendicularly to a midline of the bra from the right border of gap (120) to armhole (122) in right shoulder strap (108). As shown in FIG. 4, W2 may be greater than W3, which may be greater than W1.

Figure 6A:
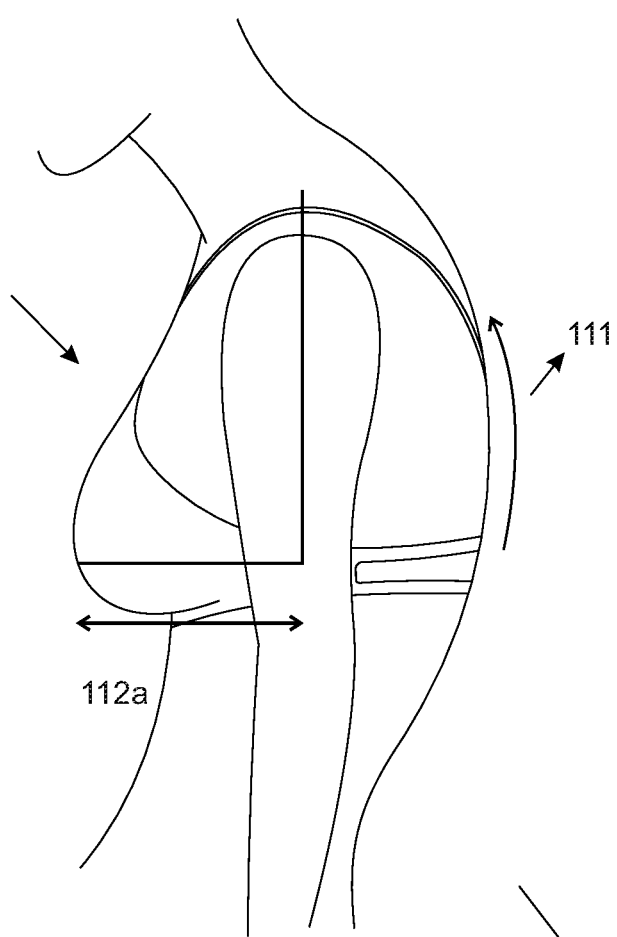
Figure 6B:
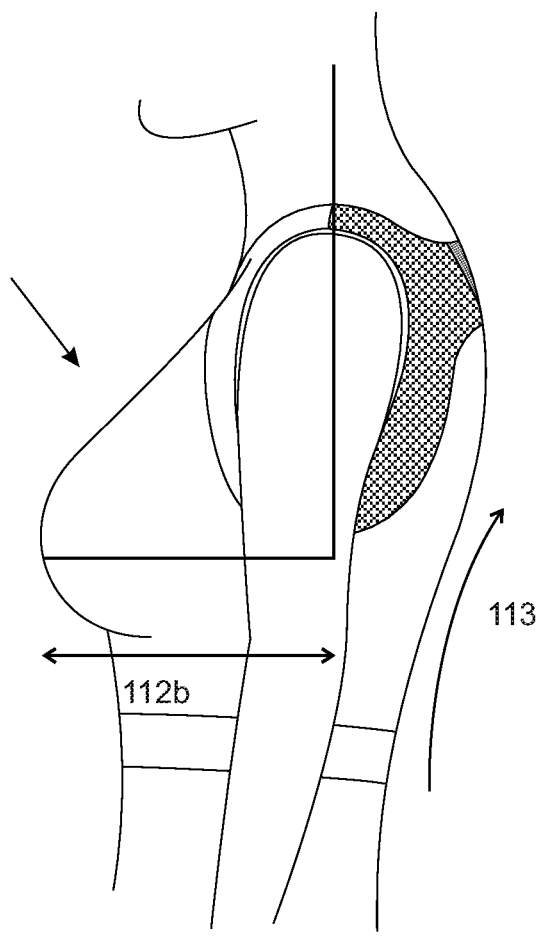

FIGS. 6a and 6b show the effect of a regular bra versus the therapeutic inventive bra. In FIG. 6a, the wearer depicted is hunched over with kyphosis (111) and the distance between the mid-arm (as measured by the middle of the shoulder downwards) and the sternum (112a) is relatively stunted due to the kyphotic nature of the wearer. In FIG. 6b, with the wearing donning the therapeutic inventive bra, the wearer is now in an upright, anatomically correct posture. The kyphosis is gone, the lumbar is supported and straight (113) and the chest has expanded, thus highlighting the increased distance between the mid-arm (as measured by middle of the shoulder downwards) and the sternum (112b).

Figure 7:
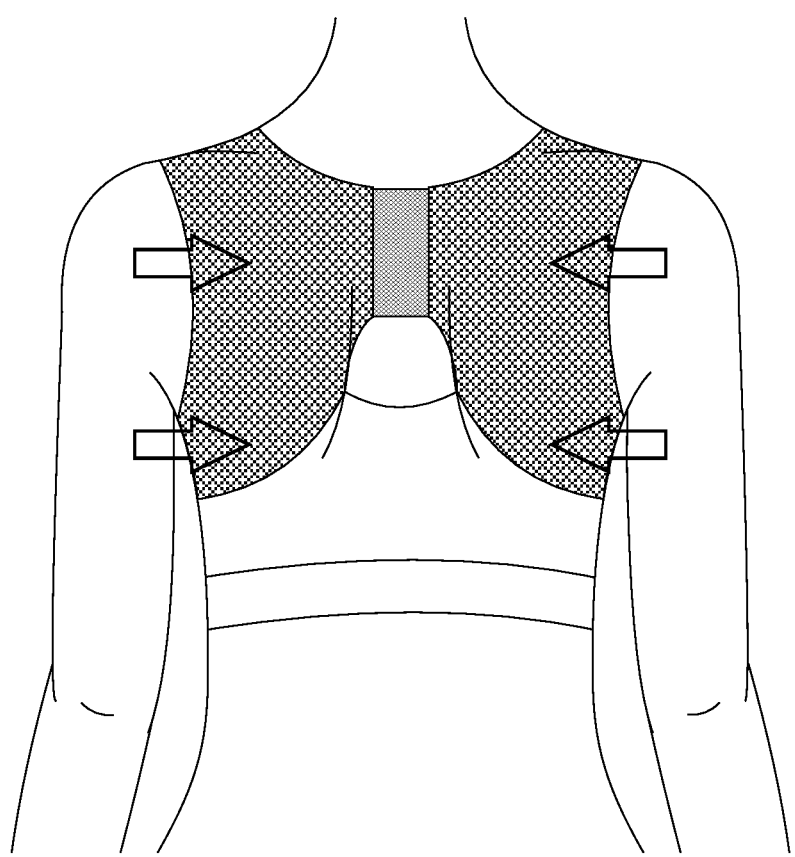
FIG. 7 is a rear view of the therapeutic bra.

FIG. 7 show the horizontal tension effects that the bra possesses—in other words, the tension is not applied downwards on the shoulders but rather horizontally on the scapulae so that the scapulae retract and bring the shoulders back along with it. This horizontal tension effect is what pinches the scapulae together and put the wearer in proper postural position.

The components of the therapeutic posture correcting and chest expanding bra (101) can further be described in terms of relative elasticity values. Elasticity, as used here, is defined as it relates to the amount of force something is pulled on. The less elastic, or more inelastic, something is, the greater the amount of tension and pull is applied. And, as it relates to posture and biomechanics, the more inelastic something is as applied to this bra, the better it helps with applying pressure in the proper biomechanical areas to place the wearer into correct posture. In other words, less elastic (more inelastic)=more tension applied. As used here, an elastic value of 1 (E1) would be more elastic than an elasticity value of 2 (E1).

Referencing the FIGS now, in order of elastic value—the elastic strap (109) has an elasticity value E4, the shoulder straps have an elasticity value E3, the chest band has an elasticity value E2, and the front and rear panels have an elasticity value E1, where E4<E3<E2<E1. Thus, the elastic strap applies the most tension and the front and rear panels apply the least amount of tension. This means that the construction and elasticity values of tension are all important in how the bra achieves biomechanically correct methods of posture correction, chest expansion, and overall posture support. For example, certain advantages can include posture recovery, spinal extension, thoracic mobility, allowing for easier breathing, reducing tension on the neck and shoulder muscles, improving back pain, and providing spinal support. Additionally, embodiments of the current invention can improve recovery from shoulder surgery, shoulder injury, physical therapy, athletic training, athletic recovery, and athletic performance as well as improving women health issues such as chronic round shoulders due to large or dense breasts and pack pain during pregnancy. These and other advantages will be apparent to those of skill in the art with the benefit of the present disclosure.

While several methods are disclosed herein, such methods are only to be limited as required by the claims. Accordingly, the various portions of the described methods can be reordered, omitted, augmented, substituted, and/or otherwise modified in any suitable manner. Variations from the description above may and can be made by one skilled in the art without departing from the scope of the invention. In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:
1. A posture correcting bra comprising:
a front panel on an anterior portion of said bra and a rear panel on a posterior portion of said bra, wherein said front panel and rear panel have an elasticity value E1;
a chest band provided along a bottom of said front panel and said rear panel, wherein said chest band and said rear panel are directly connected across the entire posterior portion of said bra, wherein said chest band has an elasticity value E2;
a left shoulder strap connecting said front panel to said rear panel, said left shoulder strap comprising a left posterior portion having an elasticity value E3;
a right shoulder strap connecting said front panel to said rear panel, said right shoulder strap comprising a right posterior portion having an elasticity value E3;
an elastic strap having an elasticity value E4 and connecting said left posterior portion of said left shoulder strap and right posterior portion of said right shoulder strap, said elastic strap comprising a top surface and a bottom surface that are substantially parallel to one another, and a left surface and a right surface that are substantially parallel to one another, wherein said right and left surfaces each have an equal length and said top and bottom surfaces each have an equal width W1 that is less than the length of said right and left surfaces, wherein said left surface is entirely connected to said left posterior portion and said right surface is entirely connected to said right posterior portion, and
a gap formed laterally between said left posterior portion, said right posterior portion, and formed vertically between said elastic strap and said rear panel;

said left posterior portion disposed along a left side of said gap and defining a left curved border of said gap;

said elastic strap disposed above said gap and defining a top border of said gap;

said right posterior portion disposed along a right side of said gap and defining a right curved border of said gap; and said rear panel disposed below said gap and defining a curved bottom border of said gap, wherein said bottom surface of said elastic strap is above said rear panel, wherein said right shoulder strap has different widths W2 and W3, wherein W2 extends perpendicularly to the right surface of the elastic strap and extends from said right surface of said elastic strap to a right armhole of said bra, and W3 extends perpendicularly to the right surface of the elastic strap and extends from said right curved border of said gap to the right armhole, wherein W2>W3>W1, and wherein E4<E3<E2<E1.

2. The bra of claim 1, wherein said front panel comprises at least two polyester fabric layers.

3. The bra of claim 1, wherein said rear panel comprises at least two polyester fabric layers.

4. The bra of claim 1, wherein said elastic strap comprises at least three fabric layers.

5. The bra of claim 4, wherein a first layer and a second layer of said at least three fabric layers are each polyester fabric and a third layer of said at least three fabric layers is a tensioning fabric.

6. The bra of claim 5, wherein said third fabric layer is between said first and second fabric layers.

7. The bra of claim 4, wherein at least two of said fabric layers are mesh fabric.

8. The bra of claim 1, wherein said left and right posterior portions each comprise at least two fabric layers.

9. The bra of claim 1, wherein said elastic strap is elastic in a horizontal direction and inelastic in a vertical direction.

10. The bra of claim 1, wherein said elastic strap is configured to reduce tension on a wearer's neck and shoulder muscles.

11. The bra of claim 1, wherein said elastic strap is pretensioned.

12. The bra of claim 1, wherein said left posterior portion of said left shoulder strap is configured to at least partially cover a region corresponding to a wearer's left scapula and said right posterior portion of said right shoulder strap is configured to at least partially cover a region corresponding to a right scapula of the wearer.

13. A garment system comprising the bra of claim 1 and an outer garment, wherein said bra is attached to an inside portion of said outer garment.

14. A therapeutic posture correcting and chest expanding bra comprising:

a front panel and a rear panel connected along a left seam and a right seam, wherein said front panel and rear panel have an elasticity value E1;

a chest band provided along a bottom of said front panel and said rear panel, wherein said chest band has an elasticity value E2;

a left shoulder strap connecting said front panel to said rear panel;

a right shoulder strap connecting said front panel to said rear panel;

said left shoulder strap further comprised of a left anterior portion and a left posterior scapular portion, wherein said left anterior portion and said left posterior scapular portion are directly connected to each other in at least two locations at opposite ends of said left shoulder strap, and said left posterior scapular portion is wider than said left anterior portion;

said right shoulder strap further comprised of a right anterior portion and a right posterior scapular portion, wherein said right anterior portion and said right posterior scapular portion are directly connected to each other in at least two locations at opposite ends of said right shoulder strap, and said right posterior scapular portion is wider than said right anterior portion;

wherein said left and right posterior scapular portions have an elasticity value E3;

an elastic strap connecting said left posterior scapular portion of said left shoulder strap and right posterior scapular portion of said right shoulder strap, wherein said elastic strap has an elasticity value E4; said elastic strap comprising a top surface and a bottom surface that are substantially parallel to one another, and a left surface and a right surface that are substantially parallel to one another, wherein said right and left surfaces each have an equal length and said top and bottom surfaces each have an equal width W1 that is less than the length of said right and left surfaces, wherein said left surface is entirely connected to said left posterior portion and said right surface is entirely connected to said right posterior portion, and a gap formed laterally between said left posterior portion, said right posterior portion, and formed vertically between said elastic strap and said rear panel;

said left posterior portion disposed along a left side of said gap and defining a left curved border of said gap;

said elastic strap disposed above said gap and defining a top border of said gap;

said right posterior portion disposed along a right side of said gap and defining a right curved border of said gap;

and said rear panel disposed below said gap and defining a curved bottom border of said gap, wherein said right shoulder strap has different widths W2 and W3, wherein W2 extends perpendicularly to the right surface of the elastic strap and extends from said right surface of said elastic strap to a right armhole of said bra, and W3 extends perpendicularly to the right surface of the elastic strap and extends from said right curved border of said gap to the right armhole;

wherein W2>W3>W1, and wherein E4<E3<E2<E1.

15. The bra of claim 14, wherein said front panel comprises two polyester fabric layers.

16. The bra of claim 14, wherein said rear panel comprises two polyester fabric layers.

17. The bra of claim 14, wherein said elastic strap comprises three fabric layers.

18. The bra of claim 17, wherein said three fabric layers include a polyester fabric layer, an elastic fabric layer, and a polyester fabric layer, respectively.

19. The bra of claim 14, wherein said left and right posterior scapular portions each comprise two fabric layers.

20. The bra of claim 14, wherein said elastic strap is elastic in a horizontal direction and inelastic in a vertical direction.

* * * * *